Figure 1:
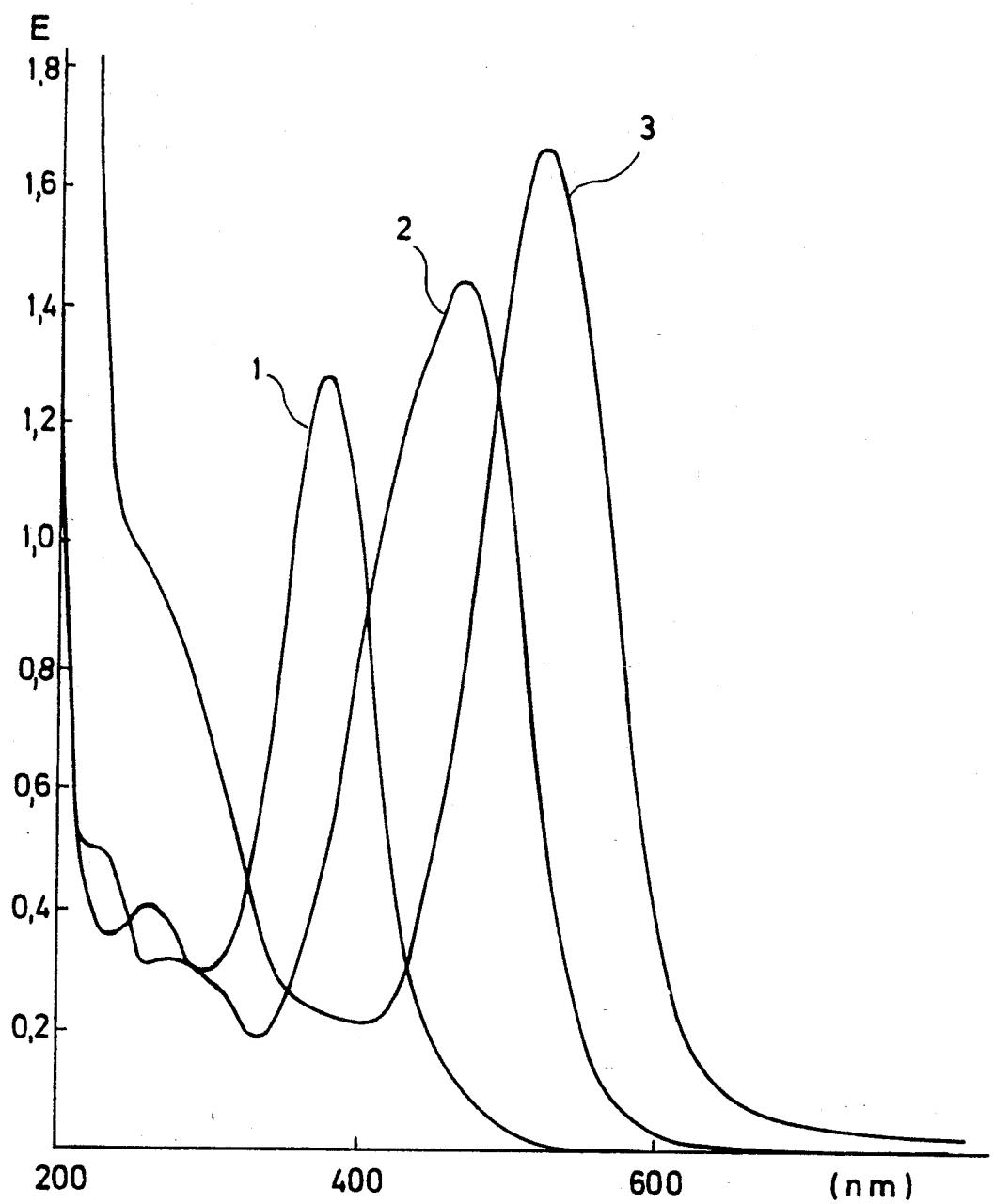

United States Patent [19]

Habenstein

[11] Patent Number: 5,077,200

[45] Date of Patent: Dec. 31, 1991

[54] AZO DYE CHROMOGENIC SUBSTRATES

[75] Inventor: Klaus Habenstein, Wetter, Fed. Rep. of Germany

[73] Assignee: Behringwerke Aktiengesellschaft, Marburg/Lahn, Fed. Rep. of Germany

[21] Appl. No.: 251,166

[22] Filed: Sep. 28, 1988

[30] Foreign Application Priority Data

Sep. 30, 1987 [DE] Fed. Rep. of Germany ....... 3732871

[51] Int. Cl.$^5$ .......................... C09B 29/42; C12Q 1/54
[52] U.S. Cl. .......................................... 435/14; 435/4; 435/18; 435/19; 435/21; 435/24; 530/300; 530/350; 530/802; 534/770; 534/771; 534/774; 534/781
[58] Field of Search ...................... 530/802; 435/4, 18, 435/21, 81, 96, 195, 130, 3; 534/795, 782, 770, 771, 774, 781

[56] References Cited

U.S. PATENT DOCUMENTS

| | | |
|---|---|---|
| 4,188,320 | 2/1980 | Kamachi et al. |
| 4,296,202 | 10/1981 | Berger et al. |
| 4,299,917 | 11/1981 | Berger et al. |
| 4,442,033 | 4/1984 | Berger et al. |
| 4,716,222 | 12/1987 | Wallenfels et al. |
| 4,797,476 | 1/1989 | Inagaki et al. |

FOREIGN PATENT DOCUMENTS

| | | |
|---|---|---|
| 550958 | 4/1986 | Australia |
| 0156347 | 3/1985 | European Pat. Off. |
| 0157384 | 3/1985 | European Pat. Off. |
| 2836644 | 3/1980 | Fed. Rep. of Germany |
| 333924 | 12/1958 | Switzerland |

OTHER PUBLICATIONS

Hellerbach et al.-Chem. Abst., vol. 70 (1969), p. 28830q.
Fuss et al.-Chem. Abst., vol. 107 (1987), p. 175, 893.
Liss-Chem. Abst., vol. 66 (1967), p. 115,564s.
Angew. Chem., vol. 98: 213-236.
Ullmanns Enzklopadie d. Techn. Chemie, 4. Auflage, vol. 8, p. 44, Verlag Chemie.

*Primary Examiner*—Sam Rosen
*Attorney, Agent, or Firm*—Finnegan, Henderson, Farabow, Garrett and Dunner

[57] ABSTRACT

Chromogenic substrates for the detection of hydrolyzing enzymes, processes for the preparation of these chromogenic substrates and the use of the chromogenic substrates.

The quantification of hydrolyzing enzymes for diagnostic purposes has to date been carried out by determination of the amounts of a fluorescent or highly absorbent chromogenic dyestuff liberated in the hydrolytic reaction, detection of which has in part been possible exlusively by instruments or in the neutral to alkaline pH range. After enzymatic hydrolysis, the chromogenic substrates according to the invention lead to highly sensitive and specifically measurable signals regardless of the pH range.

Azo dyestuff compounds with the general formula

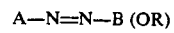

in which A) and B) have the meanings given in claim 1 and R) is a radical which can be liberated by enzymatic hydrolysis, excluding a carbonyl radical, are provided.

After enzymatic hydrolysis, highly sensitively and specifically measurable signals are obtained regardless of the pH range.

The azo dystuff compounds mentioned are used for the detection of hydrolyzing enzymes, in particular glycosidases, phosphatases and sulfatases.

12 Claims, 1 Drawing Sheet

AZO DYE CHROMOGENIC SUBSTRATES

The invention relates to chromogenic substrates for detection of hydrolyzing enzymes, processes for the preparation of these chromogenic substrates and the use of the chromogenic substrates.

Hydrolyzing enzymes, the so-called hydrolases, are responsible in the animal organism for a large number of reactions. A distinction is thereby made between hydrolases with various functions according to their specificity:

1. Esterases, such as, for example, acetylcholine esterase, which hydrolyze carbonyl esters,
2. Glycosidases, such as, for example, β-D-galactosidase, which hydrolyze the O-glycosidic linkage of sugar with one another or with alcohols,
3. Phosphatases, such as, for example, alkaline phosphatase, which hydrolyze phosphoric acid esters and
4. Sulfatases, such as, for example, iduronate sulfatase, which hydrolyze sulfuric acid esters.

The hydrolases belong to the most important enzymes of the animal organism. Their absence or reduced or increased occurrence often indicates serious diseases of the organism. A known example is mucopolysaccharidosis; this recessively inherited disease for which a distinction can be made between 7 different forms of manifestation is based on a genetically determined defect of hydrolases, for example β-galactosidase in the case of Morquio's disease and iduronate sulfate sulfatase in the case of Hunter's disease. Morquio's disease, for example, can be diagnosed unambiguously by determination of the β-D-galactosidase level of fibroblasts or leucocytes. The level of another glycosidase, amylase, in the blood or urine is used to diagnose pancreatic diseases. Hydrolytic enzymes are moreover used as diagnostic aids, so-called markers, for example in enzyme immunoassay use.

A condition of quantification of hydrolyzing enzymes for diagnostic purposes is highly sensitive and specific detection systems, so that even small enzyme concentrations can be determined exactly. Naturally occurring substrates are unsuitable for detection here, since hydrolysis products are present in the samples even before the test is carried out or the hydrolysis products are very difficult to determine. In the prior art, synthetic substrates are therefore used, the hydrolysis products of which can be detected physically or chemically. Detection is as a rule carried out by determination of the amounts of fluorescent or highly absorbent chromogenic substances liberated in the hydrolytic reaction. An almost universally applicable and therefore often used chromogenic system is that of p-nitrophenol. However, the highly pH-dependent yellow color development thereof is not without problems even for photometric evaluations and is unsuitable for visual evaluations. Fluorogenic detection systems, for example fluoresceins, or methylumbelliferones cannot be detected at all visually but only with instruments, and other chromogenic substrates, for example phenoxazines, such as are described in European Patent 156,347, and phenothiazines, in accordance with European Patent 157,384, already have a considerable intrinsic absorption in the bonded state. Again, other substrates, for example phenol derivatives and naphthol derivatives and also indoxyl, require a further chemical reaction after the hydrolytic reaction, in order to convert the chromogenic molecular group into the colored compound. Many chromogenic substrates moreover can only be used in the alkaline pH range for determination of hydrolyzing enzymes.

The present invention was therefore based on the object of providing chromogenic substrates for detection of hydrolyzing enzymes, the hydrolysis of which leads to highly sensitive and specific to measurable signals regardless of the pH range.

According to the invention, this object is achieved by a procedure in which the chromogenic substrate is an azo dyestuff compound of the general formula:

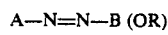
A—N=N—B (OR)

in which A) denotes a cyclic 5- or 6-membered, optionally benzo-fused radical with up to 3 hetero atoms from the group comprising N, S and O, which can optionally be substituted by halogen, nitro, alkyl, alkoxy or sulfonate groups, B) denotes an aromatic or heterocyclic ring system, such as phenyl, pyridinyl, naphthyl or quinolinyl, which can optionally be substituted by halogen, alkyl, alkoxy, dialkylamino or morpholino radicals, halogen denoting a chlorine, bromine or iodine radical, preferably a chlorine or bromine radical, and the alkyl or alkoxy groups comprising chains with 1-6 carbon atoms, preferably with 1-3 carbon atoms, and R is a radical which can be liberated by enzymatic hydrolysis, excluding a carbonyl radical.

A particularly preferred embodiment provides for the use of modified or non-modified sugar radicals or of phosphate radicals or of sulfate radicals as the radical R.

Surprisingly, it has been found that the azo dyestuff compounds according to the invention react with hydrolases of varying specificity, depending on the radical R chosen, and show a color change which can be measured both visually and photometrically in the alkaline and in the acid pH range, and the color change in the acid pH range can be intensified significantly by complexing.

Although the use of chromogenic azo dyestuff compounds of the general formula given for detection of leucocyte esterases is already known from German Offenlegungsschrift 2,836,644, the substrates here are exclusively for carbonyl esterases in which the radical R denotes a carboxylic acid radical or an aminoacid or peptide radical provided with a nitrogen-protective group customary in peptide chemistry. Moreover, only use in the alkaline pH range is described for these azo dyestuff compounds.

By suitable choice of the groups A and B in the general formula

A—N=N—B (OR)

tailor-made substrates can be prepared for specific analytical problems. A) here can be a cyclic 5- or 6-membered, optionally benzo-fused radical with up to 3 hetero atoms from the group comprising N, S and O, which can optionally be substituted by halogen, nitro, alkyl, alkoxy or sulfonate groups, whilst B) can be an aromatic or heterocyclic ring system, such as phenyl, pyridinyl, naphthyl or quinolinyl, which can optionally be substituted by halogen, alkyl, alkoxy, dialkylamino or morpholino radicals. The halogen radical can thereby be a chlorine, bromine or iodine radical, preferably a chlorine or bromine radical; the methyl or alkoxy groups comprise chains with 1-6 carbon atoms, preferably with 1-3 carbon atoms. Depending on the choice of the groups A and B, the free chromogens have a high color intensity, i.e. a high molar extinction coefficient, which thus renders highly sensitive enzyme assays possible. Particularly preferred azo dyestuffs here are those of which the compounds, i.e. the bonded chromogens, which represent the chromogenic substrates, have as little color as possible, whilst the free chromogen, i.e. the azo dyestuff liberated from the azo dyestuff compound by hydrolysis, is very deeply colored. For example, colorless to cream-colored galactosides which are reacted by hydrolysis to give red-violet to blue free chromogens can be prepared. Overlapping of the absorption spectra of the bonded chromogen and the free chromogen is moreover as low as possible in preferred chromogenic substrates according to the invention. The solubility of the chromogenic substrate is another parameter which greatly depends on the choice of the groups A and B and on which extremely different requirements are imposed, depending on the intended use of the chromo-genic substrate. Thus, a good solubility of the chromo-genic substrate and free chromogen in aqueous media is required if the quantification of the reaction is to be by photometry, whereas carrier-bonded chromogenic substrates, for example after fixing to paper or films, require chromogens with a low solubility in aqueous media in order to reduce bleeding in aqueous solution.

Particularly preferred are chromogenic substrates leading to chromogenes after hydrolysis which display a bathochronic color shift by complexation with suitable metal ions.

Particularly suitable chromogenic substrates are substrates of the abovementioned general formula in which A—: contains the structure

in which the carbon atom shown is the constituent of A bonded to the diazo group
and
—B (OR): contains the structure

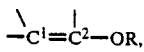

in which the carbon atom $C^1$ shown is the constituent of B bonded to the diazo group, in which A, B and R have the meaning given in claims 1 and/or 2. By the change in absorption due to complexing, these substrates have an effect beyond that which can be achieved by hydrolysis of the chromogenic substrate. This effect remarkably occurs both in the acid and in the alkaline pH range.

Particularly preferred azo dyestuffs are
5-nitrothiazole-2-azo-4'-phenol
benzothiazole-2-azo-4'-phenol
6-nitrobenzothiazole-2-azo-4'-phenol
thiazole-2-azo-2'-pyridin-3'-ol
4,5-dimethylthiazole-2-azo-2'-pyridin-3'-ol
6-ethoxybenzothiazole-2-azo-2'-pyridin-3'-ol
benzothiazole-2-azo-2'-pyridin-3'-ol
5-bromothiazole-2-azo-2'-pyridin-3'-ol
5-chlorothiazole-2-azo-2'-(4'-methylphenol)
thiazole-2-azo-6'-(2'-bromo-3'-hydroxypyridine)
4,5-dimethylthiazole-2-azo-6'-(2'-bromo-3'-hydroxypyridine)
6-ethoxybenzothiazole-2-azo-6'-(2'-bromo-3'-hydroxypyridine)
4'-cyanopyrazole-3-azo-2'-(4'-methoxyphenol)
5-nitrophenylsulfonylthiazole-2-azo-2'-(4'-methylphenol)
4,5-dimethylthiazole-2-azo-2'-(5'-chloro-3'-hydroxypyridine)
thiazole-2-azo-2'-(4'-morpholinophenol).

For the preparation of the compounds of the general formula given according to the invention, the azo dyestuff with the particular groups A and B desired is first prepared in a manner which is known per se by processes which are known from the literature. Examples and literature for customary preparation processes are to be found, for example, in Ullmanns EnzyklopUädie der Technischen Chemie (Ullmann's Encyclopedia of Industrial Chemistry), 4th edition, Verlag Chemie, Volume 8, page 244.

Chromogenic substrates for the detection of phosphatases and sulfatases can be prepared by reacting the corresponding azo dyestuffs with suitable acid halides. To prepare phosphatase substrates, an azo dyestuff is usually reacted with phosphorus oxychloride, whilst the azo dyestuff is reacted with chlorosulfonic acid for the preparation of sulfatase substrates.

To prepare glycosides, the azo dyestuffs are glycosilated by processes which are also known. β-Galactosides can be prepared, for example, by reaction of the corresponding azo dyestuffs with α-D-acetobromogalactose and subsequent deacetylation. Glycosilating processes are described, for example, in Angewandte Chemie 98 (1986) pages 213-236 and the literature quoted therein. Examples of the glycosides obtainable by the processes mentioned are, for example, α- and β-D-galactopyranosides, α- and β-D-glucopyranosides and the oligosaccharide derivatives derived therefrom with 2-10, preferably 3-7, monosaccharide units.

The chromogenic substrates according to the invention are used for the detection of various hydrolytic enzymes, for example phosphatases, sulfatases and glycosidases. For the enzyme detection, the chromogenic substrate is provided in a reagent mixture which can contain, if appropriate, the necessary buffer substances, stabilizers, activators, solubilizing agents, auxiliary enzymes or other auxiliary chemicals. If their stability and chemical compatibility is adequate, the various individual chemicals can be present side by side in a solution, but they can also first be mixed with one another shortly before the detection reaction. The actual detection of the hydrolytically active enzyme then takes place by measurement of the extinction of the azo dyestuff liberated by the enzyme-catalyzed hydrolysis from the corresponding azo dyestuff compound after the reagent mixture has been brought together with the hydrolyzing enzyme to be detected or the biological sample to be tested. Reaction in solution is preferred here, and if appropriate can be carried out directly in a cell and evaluated immediately by subsequent recording of the signal by transmitted photometry. Application of the chromogenic substrates according to the invention to fibrous or film-like reagent carriers which allow recording of the signal by reflectance photometry after the reaction has been carried out is also preferred. In both cases, visual evaluation is likewise possible when the chromogenic substrates according to the invention are used.

The chromogenic substrates according to the invention can be provided in various forms. Embodiment forms which already contain a combination of the chromogenic substrates according to the invention with the additional reagents needed for the test are preferred. Examples of these are solutions, reagent tablets, powder mixtures or lyophilisates, if the detection reaction is subsequently to be carried out in solution. Alternatively, the chromogenic substrates can also be absorbed onto absorbent carriers or incorporated into hydrophilic films which take up water, together with the additional reagents needed for the test.

The invention is illustrated by the following figure and the examples. FIG. 1

The figure illustrates the change in the absorption maximum of a chromogenic substrate, i.e. thiazole-2-azo-2'-pyridin-3'-ol (tap).

The peak at 376 nm here (spectrum 1) corresponds to the azo dyestuff galactoside, the absorption maximum at 468 nm (spectrum 2) corresponds to the free chromogen, and finally the absorption maximum at 526 nm (spectrum 3) corresponds to the copper complex of the free chromogen. Comparison of the spectra for the galactoside and the copper complex clearly shows that the corresponding absorption curves do not overlap.

EXAMPLE 1

Preparation of thiazole-2-azo-2'-pyridin-3'-ol (tap)

Diazotization 5 g (50 mmol) of 2-aminothiazole are dissolved in 75 ml of half-concentrated hydrochloric acid. 30 ml of sodium nitrite solution (117 g/l=1.7 mole/l) are added dropwise at 0° to 4° C. in the course of 30 minutes, with stirring. When the addition has ended, the reaction mixture is stirred for 30 minutes.

Coupling 4.3 g (45 mmol) of 3-hydroxypyridine are dissolved in 500 ml of 0.1 M NaOH and the solution is cooled to 0 to 5° C. with ice cubes. This temperature is maintained until the coupling has ended.

Under pH control, the similarly cooled diazonium salt is added dropwise to the pyridinol solution. The pH is kept between pH 7 and pH 10 during the coupling by dropwise addition of 10 M sodium hydroxide solution.

Isolation

When the coupling has ended, the solution is brought to pH 3 with concentrated hydrochloric acid, and the precipitate formed is filtered off with suction and dried in a desiccator over phosphorus pentoxide in vacuo.

Purification

After comminution, the dry crude product is extracted in a Soxhlet apparatus with 1 l of toluene. The tap which has crystallized out in the flask is filtered off with suction and then if appropriate recrystallized several times from toluene and/or water. Red-brown needles are formed on slow cooling.

The yield after the purification was about 1.5 g of tap.

Characterization

The resulting product was characterized by thin layer chromatography, melting point determination and NMR spectroscopy.

A: Thin layer chromatography: mobile phase chloroform/ methanol 90/10 on silica gel plates from Merck; Rf value of 0.38.
B: The melting point determination showed a melting point mp>170° C., with decomposition
C: NMR spectroscopy: The NMR spectrum had the following peaks:
  1. Doublet at 8.4 ppm coupled with 5.
  2. Doublet at 8.2 ppm coupled with 4.
  3. Doublet at 8.1/8.2 ppm coupled with 5.
  4. Doublet at 7.9 ppm coupled with 2.
  5. Quadruplet at 7.5/7.6 ppm coupled with 1. and 3.
  6. Several individual peaks from 1.5 to 5.5 ppm.

According to the integration curve, each position represents a hydrogen atom.

EXAMPLE 2

Preparation of 5-nitrothiazole-2-azo-4'-phenol (nitrotaph)

Diazotization 3.0 g (20 mmol) of 2-amino-5-nitrothiazole are dissolved in 40 ml of 50% strength sulfuric acid, with gentle warming. The dark brown solution is cooled to −20° C. in a double-walled reaction vessel which can be temperature-controlled. This temperature is maintained during the diazotization and must not rise above −15° C. during the addition of 7 g (20 mmol) of nitrososulfuric acid, which takes about 20 minutes. After the addition of nitrososulfuric acid, the reaction mixture is stirred at −20° C. for a further 2 hours.

Coupling 1.8 g (20 mmol) of phenol are dissolved in about 200 ml of 0.1M NaOH in a double-walled reaction vessel which can be temperature-controlled, and the solution is cooled to 0° C. The diazonium salt is added dropwise from its temperature-controlled reaction vessel into the phenol solution while maintaining this temperature.

Isolation

The salt which has precipitated is filtered off with suction and washed with ethyl acetate. The aqueous mother liquor is extracted by shaking with 800 ml of ethyl acetate. The ethyl acetate phases are combined, pre-dried with sodium sulfate and evaporated to dryness on a rotary evaporator.

Purification

The dry crude product is boiled under reflux twice for 30 minutes with 50 ml of toluene each time. After cooling and filtering, 1.6 g of red-brown product remain. This product is dissolved in 150 ml of ethyl acetate, with heating, and the solution is filtered. The filtrate is transferred to a 1 l column (6 cm diameter) with silica gel and eluted with ethyl acetate/glacial acetic acid (99/1).

The yield after evaporation to dryness, on a rotary evaporator, of the fractions combined according to the result of thin layer chromatography control was 1.2 g of 5-nitrothiazole-2-azo-4'-phenol.

Characterization

The resulting product was characterized by thin layer chromatography and melting point determination.

A. Thin layer chromatography: The thin layer chromatography analysis in three different systems showed that the product obtained was uniform.

The thin layer chromatography was carried out with
1. Chloroform/methanol 90/10
2. Ethyl acetate/glacial acetic acid 99/1
3. Methylene chloride/glacial acetic acid 90/10

The Rf value was determined only for the chloroform/methanol system and was Rf = 0.49.

B. The melting point determination showed a melting point mp > 200° C.

TABLE 1

Hydroxy dyestuffs prepared analogously to the processes described in Examples 1 and 2

| Azo dyestuff | Extinction maximum (nm)/pH Acid | Extinction maximum (nm)/pH Salt | $\varepsilon_{mol}/\lambda_{max}$ Salt (nm) |
|---|---|---|---|
| 5-nitrothiazole-2-azo-4'-phenol | 430/6 | 590/11 | 54,000/590 |
| benzothiazole-2-azo-4'-phenol | 360/8 | 510/11 | 45,000/510 |
| 6-nitrobenzothiazole-2-azo-4'-phenol | 490/7 | 550/9 | 40,000/550 |
| thiazole-2-azo-2'-pyridin-3'-ol | 376/4 | 468/6 | 22,000/468 |
| 4,5-dimethylthiazole-2-azo-2'-pyridin-3'-ol | 425/6 | 480/7 | 41,000/480 |
| 6-ethoxybenzothiazole-2-azo-2'-pyridin-3'-ol | 440/5 | 500/7 | 17,000/500 |
| benzothiazole-2-azo-2'-pyridin-3'-ol | 390/5 | 490/7 | 24,000/490 |
| 5-bromothiazole-2-azo-2'-pyridin-3'-ol | 410/5 | 490/7 | 21,000/490 |
| 5-chlorothiazole-2-azo-2'-(4'-methylphenol) | 400/8 | 550/9 | 20,000/550 |
| thiazole-2-azo-6'-(2'-bromo-3'-hydroxypyridine) | 400/4 | 470/6 | 25,000/470 |
| 4,5-dimethylthiazole-2-azo-6'-(2'-bromo-3'-hydroxypyridine) | 440/4 | 490/6 | 32,000/490 |
| 6-ethoxybenzothiazole-2-azo-6'-(2'-bromo-3'-hydroxypyridine | 400/4 | 500/6 | 32,000/500 |
| 4-cyanopyrazole-3-azo-2'-(4'-methoxyphenol) | 320/1 | 430/7 | 13,000/430 |
| 5-nitrophenylsulfonyl-thiazole-2-azo-2'-(4'-methylphenol) | 370/7 | 570/9 | 21,000/570 |
| 4,5-dimethylthiazole-2-azo-2'-(5'-chloro-3'-hydroxypyridine | 420/./. | 490/./. | 36,600/490 |
| thiazole-2-azo-2'-(4-morpholinophenol) | 470/./. | 460/./. | 18,000/460 |

In addition to the examples listed here, other derivatives, containing hydroxyl groups, of the substance classes of naphthols and hydroxyindoles were used as coupling components. The amine components used for the diazothization can be seen from the following list: aminothiazoles (inter alia substituted by alkyl, halogen- or nitro-phenyl groups), aminobenzothiazole derivatives, aminopyridine derivatives, aminothiadiazole derivatives, aminoisothiazole derivatives, aminooxazole and aminoisoxazole derivatives, aniline derivatives and aminonaphthalene derivatives.

EXAMPLE 3

Complexing of hydroxyazo dyestuffs.

The complexing properties of various compounds were investigated as follows:

The following were pipetted into a cell in the sequence shown and stirred immediately:

2.960 m of 0.1M phosphate buffer pH 7, 30 ul of a 10 μM solution of the azo dyestuff in methanol and 10 ul of a 0.1M aqueous solution of the complexing metal ion.

Qualitative information was obtained as follows:

A methanolic solution of the compound investigated was added to an indicator paper preimpregnated with 0.1M phosphate buffer solution pH 7 and dried. After drying, a 0.3 mM solution of the complexing metal ion was dripped onto the paper.

FIG. 1 shows an example of the color shift by complexing.

Further examples are summarized in Table 2.

TABLE 2

Complexing of hydroxyazo dyestuffs

| Azo dyestuff | Complexing atom | $\varepsilon_{mol}/\lambda_{max}$ |
|---|---|---|
| Thiazole-2-azo-2'-pyridin-3-ol | Cu | 27,550/526 |
| | Co | 25,000/490 |
| | Ni | 32,000/500 |
| 4,5-Dimethylthiazole-2-azo-2'-pyridin-3'-ol | Cu | 46,000/538 |
| Benzothiazole-2-azo-2-pyridin-3'-ol | Cu | 25,000/540 |
| 5-Chlorothiazole-2-azo-2'-pyridin-3'-ol | Cu | 16,000/540 |
| 4-Cyanopyrazole-3-azo-2'-(4'-methoxyphenol) | Cu | 17,000/620 |
| 5-Bromothiazole-2-azo-2'-pyridin-3'-ol | Cu | 29,000/550 |
| 4,5-Dimethylthiazole-2-azo-2'-(5'-chloro-3'-hydroxypyridine) | Cu | 38,300/540 |
| Thiazole-2-azo-2'-(4'-morpholinophenol) | Cu | 33,400/550 |

EXAMPLE 4

Glycosylating reactions

A. Galactosylation of thiazole-2-azo-2'-pyridin-3'-ol (tap)

2.06 g (0.01 mole) of tap, 4.1 g (0.01 mole) of acetobromogalactose, 1.15 g (5 mmol) of Ag20 and 1.45 g (0.01 mole) of calcium sulfate . ½ H2O are heated under reflux in 100 ml of dried toluene in a dry apparatus.

The reaction is carried out with exclusion of light and water (calcium chloride drying tube on the condenser), with stirring.

After a reaction time of 2 hours, the reaction is controlled by thin layer chromatography. The tap acetogalactoside formed appears as a yellow spot above the tap spot. Mobile phase chloroform/ethyl acetate 4/1 and chloroform/acetone 4/1.

If the reaction is not sufficient, acetobromogalactose and Ag2O are added again and the mixture is heated again under reflux.

When the reaction has taken place, the batch solution is filtered, the filter is washed with toluene and the wash toluene and mother liquor are combined and concentrated on a rotary evaporator at a maximum bath temperature of 40° C. under about 70 millibar.

The residue is dried at room temperature under 200 mbar in a vacuum drying cabinet. The contaminated product is purified by column chromatography (separating agent silica gel 40, 0.06–0.2 mm, mobile phase chloroform/ethyl acetate 4/1). The purified tap tetraacetylgalactoside is dried and its purity is checked by thin layer chromatography.

B. Deacetylation of the acetyl glycoside formed

The deacetylation is carried out in anhydrous methanol with sodium methylate. For this, the acetyl glycoside is dissolved in methanol to a concentration of 2 mg/ml and a little sodium methylate is added (5–10 μl of a 30% strength methanolic solution). The course of the deacetylation is monitored by means of thin layer chromatography.

Mobile phase: chloroform/ethyl acetate 4/1 and chloroform/methanol 3/1.

When the reaction has gone to completion, the solution is rendered neutral to weakly acidic with the ion exchanger Dowex 50×8.

The solution is then concentrated and the residue is dried. The yield of tap β-galactoside was 180 mg.

C. Glucosilation of 3,5-dimethylthiazole-2-azo-2'-pyridin-3'-ol (dimetap)

2.63 g (0.01 mole) of Brigl's anhydride and 2.36 g (0.01 mole) of dimetap are heated under reflux in 100 ml of toluene, while stirring and with the exclusion of water.

Reaction time: 24–48 hours.

The reaction is checked by thin layer chromatography.

Mobile phase: chloroform/ethyl acetate 4/1.

The deacetylation is carried out as described under B.

The yield was 200 mg of dimetap β-glucoside.

EXAMPLE 5

Reaction of chromogenic galactosides with β-galactosidases

Thiazole-2'-azo-2'-pyridin-3'-β-galactoside (tap-gal) was degraded with β-galactosidases from E.coli (EC 3.2.1.22, pH optimum about 7.2) and Asp.oryzae (EC 3.2.1.23, pH optimum about 4.5), Calbiochem GmbH. The degradation was monitored visually and photometrically. For comparison, the degradation rates of the known chromogenic β-galactosidase substrates resorufin β-galactoside (resgal) and chlorophenol red β-galactoside (CPR-gal) were determined in parallel.

Photometric method 1 ml of a 0.1M buffer solution (phosphate buffer pH 7 or acetate buffer pH 4.5) is mixed with 0.1 ml of the particular substrate solution (2.5 mmol/l or 10 mmol/l) in a cell with an optical path of 1 cm and the degradation reaction is started by addition of 10 μl of a β-galactosidase solution (840 U/l). The degradation reaction is monitored for about 10 minutes. At pH 4.5, the tap solution still contains 0.33 mmol/l of copper nitrate, and the other two substrates are measured after rebuffering to pH 7.

TABLE 3

Results of the photometric investigations

Degradation rate (μmol/minute) at various substrate concentrations

| Chromogenic substrate | 0.25 (mmol/l) | | 1.0 (mmol/l) | |
|---|---|---|---|---|
| | E. coli | Asp. orycae | E. coli | Asp. orycae |
| tap-gal | 0.35 | 0.7 | 0.6 | 1.5 |
| res-gal | 0.4 | 1.1 | 0.2* | ./.* |
| CPR-gal | 0.27 | 0.15 | 0.57 | 0.49 |

*Because of the poor solubility of this substrate in water, a considerable amount of methanol/dimethylformamide must be added, which then inhibits the enzymes.

Visual method

Indicator paper was preimpregnated with a 0.1M buffer solution (phosphate buffer pH 6, pH 7 or pH 7.8 or citrate buffer pH 4.5), dried, after-impregnated with a methanolic solution of 1 g/l of the particular substrate and dried. The papers intended for tap-gal additionally contained 0.3 mmol/l of copper nitrate in the buffers pH 4.5, pH 6 and pH 7.

The galactosidase test papers thus obtained were dipped in aqueous solutions of decreasing galactosidase concentration and the color development was compared against a blank value. Table 4 contains the minimum concentrations of enzyme still detectable, the system being rebuffered to pH 7 before being read for res-gal and CPR-gal where the previous reaction was carried out at pH 4.5 or pH 6.

TABLE 4

Maximum sensitivity of chlorophenol red galactoside (CPR). resorufin galactoside (res) and thiazolylazopyridinol galactoside (tap) in the dipping test in U/l

| Enzyme | Buffer | pH | Test duration (min) | Substrate | | | |
|---|---|---|---|---|---|---|---|
| | | | | CPR | res | tap | tap + Cu++ |
| E. coli Galactosidase | Phosphate | 7.8 | 1 | 840 | 840 | 840 | ./. |
| | | | 4 | 210 | 210 | 210 | ./. |
| A. orycae Galactosidase | Citrate | 4.5 | 1 | ./. | 240 | ./. | 240 |
| | | | 4 | 500 | 60 | | 60 |
| | Phosphate | 6 | 1 | 2.400 | 240–480 | ./. | 240–480 |
| | | | 4 | 800 | 120 | | 120 |
| | Phosphate | 7 | 1 | ./. | 960 | ./. | 960 |
| | | | 4 | 2.000 | 240 | | 240 |

EXAMPLE 6

Reaction of 4,5-dimethylthiazole-2-azo-2'-pyridine-3'-8-D-glucopyranoside (dimetap-gluc) with β-glucosidase (EC 3.2.1.21).

2.9 ml of 0.1 M phosphate buffer pH 7 are mixed with an aqueous solution, containing 1.0 g/1, of dimetap-gluc and 0.1 ml of a 10 mM copper nitrate solution in a cell with an optical path of 1 cm and the reaction is started by addition of 0.1 ml of a β-glucosidase solution (Calbiochem GmbH). After a reaction time of 15 minutes, the substrate is completely split into free chromogen and glucose (photometric control).

EXAMPLE 7

Preparation and reaction of 5-nitrothiazole-2-azo-4'-phenyl phosphate (nitrotaph-phosphate)

Preparation 150 mg (0.6 mmol) of nitrotaph were dissolved in 2.5 ml of dry pyridine and the solution was cooled with ice. After addition of 200 ul (2.2 mmol) of phosphorus oxychloride, the mixture was stirred for 6 hours, while cooling with ice, and then stored in a refrigerator for 18 hours.

Isolation

The pyridine was distilled off on a rotary evaporator in a waterbath at 40° C. 5 g of ice were added to the residue. After the ice had melted, the solution was brought to pH 7 with 2M potassium hydroxide solution and evaporated to dryness.

Twice more, 10 ml portions of analytical grade ethanol were then added to the crude product and the mixture was concentrated to dryness.

Purification 40 mg of crude product were dissolved in 1 ml of a water/methanol mixture and purified on a preparative silica gel plate (Merck) (mobile phase: ethyl acetate/methanol/water 20/5/5).

Reaction with alkaline phosphatase (E.C. 3.1.3.1.)

The substrates indoxyl phosphate and nitrotaph phosphate were used in an optimized photometric method for the determination of alkaline phosphatase. Table 5 contains the test conditions and results of this method.

TABLE 5

| Test concentration μmol/l | Test of the alkaline phosphatase U/l | Test activity and Hg 623 mm mE/minute | Hg 578 mm |
|---|---|---|---|
| Nitrotaph-phosphate | 19 | 199 | 89 |
| | 65 | 199 | 265 |
| Indoxyl phosphate | 4,900 | 95 | 99 |

Test conditions:
Glycine buffer  0.1 mol/l pH 10.5
 0.1 mmol/l Zn++
 1 mmol/l mg++

EXAMPLE 8

Preparation and reaction of 5-nitrothiazole-2-azo-4'-phenyl sulfate (nitrotaph sulfate)

Preparation 0.84 ml (12.5 mmol) of chlorosulfonic acid were slowly added dropwise to 5 ml of pyridine, with stirring; the mixture was thereby cooled with an ice-sodium chloride mixture. 500 mg of nitrotaph were introduced into the suspension formed and the mixture was stirred at 40° C. in a waterbath. After 25 hours, 20 ml of water were added to the reaction mixture and the mixture was neutralized with 2M potassium hydroxide solution and concentrated to dryness on a rotary evaporator.

Purification 150 mg of crude product were dissolved in a water-/methanol mixture and separated on a preparative silica gel plate (Merck).
Mobile phase: ethyl acetate/water/methanol 100/25/30 (Rf about 0.4).

Reaction with arylsulfatase (E.C. 3.1.6.1)

The nitrotaph-sulfate was dissolved from the silica gel with methanol (eluate). Filterpaper was impregnated with 0.1M acetate buffer pH 6.2 and dried. Various dilutions of the eluate were dripped onto the paper and incubated with arylsulfatase (Boehringer Mannheim). An easily visible color change from yellow to green took place with 80 U/l within 1 minute.

I claim:

1. A chromogenic substrate for detection of a hydrolyzing enzyme, wherein the chromogenic substrate is an azo dye-stuff compound of the formula:

A—N=N—B (OR) 

in which
  a) denotes a cyclic 5- and 6-membered, optionally benzo-fused radical with up to 3 hetero atoms from the group consisting of N, S and O, which can optionally be substituted by halogen, nitro, alkyl, alkoxy or sulfonate groups;
  B) denotes pyridinyl which can optionally be substituted by halogen, alkyl, alkoxy, dialkylamino or morpholino radicals and
  R) is a radical which can be liberated by enzymatic hydrolysis, and is a radical selected from the group consisting of sugar, phosphate and sulfate.

2. A chromogenic substrate as claimed in claim 1, wherein the product of the hydrolysis of the chromogenic substrate is suitable for the formation of complexes with metal ions.

3. A chromogenic substrate as claimed in claim 2, wherein
A—: contains the structure

in which the carbon atom shown is the constituent of A bonded to the diazo group,
and
—B (OR): contains the structure

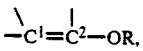

in which the carbon atom C¹ shown in the constituent of B bonded to the diazo group.

4. A chromogenic substrate as claimed in claim 1, which is an azo dyestuff selected from the group consisting of:
  thiazole-2-azo-2'-pyridin-3'-ol
  4,5-dimethylthiazole-2-azo-2'-pyridin-3'-ol
  6-ethoxybenzothiazole-2-azo-2'-pyridin-3'-ol
  benzothiazole-2-azo-2'-pyridin-3'-ol
  5-bromothiazole-2-azo-2'-pyridin-3'-ol
  thiazole-2-azo-6'-(2'-bromo-3'-hydroxypyridine)
  4,5-dimethylthiazole-2-azo-6'-(2'-bromo-3'-hydroxypyridine)
  6-ethoxybenzothiazole-2-azo-6'-(2-bromo-3'-hydroxypyridine), and
  4,5-dimethylthiazole-2-azo-2'-(5'-chloro-3'-hydroxypyridine).

5. A process for the preparation of a chromogenic substrate as claimed in claim 1, which comprises reacting an azo dyestuff of the formula:

A—N=N—B (OR) 

with an acid halide or glycosylating the azo dyestuff.

6. The process for the preparation of a chromogenic substrate as claimed in claim 5, wherein an azo dyestuff of the formula:
A—N=N—B (OR) 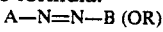

is reacted with acetobromogalactose and then with sodium methylate.

7. A method of using a chromogenic substrate as claimed in claim 1 for detection of a hydrolyzing enzyme, in which R is a phosphate radical, for the detection of a phosphatase, comprising the steps of (a) providing the chromogenic substrate in a reagent mixture; and (b) detecting the phosphatase by measurement of the extinction of the azo dyestuff compound liberated by the resulting enzyme-catalyzed hydrolysis.

8. A method of using a chromogenic substrate as claimed in claim 1, in which R is a sulfate radical, for the detection of a sulfatase, comprising the steps of (a) providing the chromogenic substrate in a reagent mixture; and (b) detecting the sulfatase by measurement of the extinction of the azo dyestuff compound liberated by the resulting enzyme-catalyzed hydrolysis.

9. A method of using a chromogenic substrate as claimed in claim 1, in which R is a modified or non-modified sugar radical, for the detection of a glycosidase, comprising the steps of (a) providing the chromogenic substrate in a reagent mixture; and (b) detecting the glycosidase by measurement of the extinction of the azo dyestuff compound liberated by the resulting enzyme-catalyzed hydrolysis.

10. A reagent mixture for the detection of a hydrolyzing enzyme, containing one or more chromogenic substrates as claimed in claim 1 and at least one of the following substances selected from the group consisting of
buffer substances,
stabilizers,
activators,
solubilizing agents, and
auxiliary enzymes.

11. A reagent mixture as claimed in claim 10, in which the chromogenic substrate is made available in solution, as a reagent tablet, as a buffer mixture or as a lyophilisate, together with additional reagents needed for the test.

12. A reagent mixture as claimed in claim 10, in which the chromogenic substrate is absorbed onto an absorbent carrier or incorporated into a hydrophilic film, in combination with additional reagents needed for the test.

* * * * *